(12) United States Patent
Nakamura et al.

(10) Patent No.: US 6,765,098 B1
(45) Date of Patent: Jul. 20, 2004

(54) FULLERENE DERIVATIVES

(75) Inventors: Eiichi Nakamura, 5-3-3-1001, Honkomagome, Bunkyo-ku, Tokyo 113-0021 (JP); Masaya Sawamura, Tokyo (JP); Hiroyuki Isobe, Tokyo (JP)

(73) Assignees: Fujisawa Pharmaceutical Co., Ltd, Osaka (JP); Eiichi Nakamura, Tokyo (JP)

( * ) Notice: Subject to any disclaimer, the term of this patent is extended or adjusted under 35 U.S.C. 154(b) by 0 days.

(21) Appl. No.: 09/622,915
(22) PCT Filed: Mar. 10, 1999
(86) PCT No.: PCT/JP99/01146
    § 371 (c)(1),
    (2), (4) Date: Nov. 17, 2000
(87) PCT Pub. No.: WO99/46235
    PCT Pub. Date: Sep. 16, 1999

(30) Foreign Application Priority Data

Mar. 10, 1998 (JP) .......................................... 10-058614

(51) Int. Cl.[7] ..................... C07D 233/90; C07D 211/90; C07C 69/76; C07C 63/33
(52) U.S. Cl. .................... 548/338.1; 546/186; 560/101; 562/441; 562/442; 562/488
(58) Field of Search ...................... 548/338.1; 546/186; 560/101; 562/441, 442, 488; 423/414, 445 B

(56) References Cited

U.S. PATENT DOCUMENTS

| 5,310,669 A | * | 5/1994 | Richmond et al. ........... 435/177 |
| 5,679,861 A | | 10/1997 | Kuo et al. |
| 6,162,926 A | * | 12/2000 | Murphy et al. .............. 548/417 |
| 6,204,391 B1 | * | 3/2001 | Friedman et al. ......... 548/338.1 |

FOREIGN PATENT DOCUMENTS

| DE | 43 12 475 | | 10/1994 |
| EP | 0 770 577 | | 5/1997 |
| EP | 0 919 520 | | 6/1999 |
| WO | WO 94/25424 | | 11/1994 |
| WO | WO 95/09564 | | 4/1995 |
| WO | WO-95/19949 | * | 7/1995 |
| WO | WO 96/09275 | | 3/1996 |
| WO | WO 96/36631 | | 11/1996 |

OTHER PUBLICATIONS

Eiichi Nakamura et al, Biological Activity of Water–Soluble Fullerenes. Structural dependence of DNA Cleavage, Cytotoxicity, and Enzyme Inhibitory Activities Including HIV–Protease Inhibition, Bull. Chem: Soc. Jpn., 69, 2143–2151 (1996).*

Simon H. Friedman et al, Inhibition of the HIV–1 Protease by Fullerence Derivatives: Model Building Studies and Experimental Verification, J. Am. Chem. Soc. 1993, 115, 6506–6509.*

A. M. Cassell, et al., Angew. Chem. Int. Ed., vol. 37, pp. 1528–1531 (1998).

S. Asayama, et al., Bioconjugate Chem. vol. 8, No. 6, XP–000725212, pps. 833–838, "Design of Comb–Type Polyamine Copolymers for a Novel pH–Sensitive DNA Carrier," Nov. 1, 1997.

Y. Yoshikawa, et al., FEBS Letters, vol. 361, No. 2,3, XP–001000181. pps. 277–281, "Diaminoalkanes with an Odd Number of Carbon Atoms Induce Compaction of a Single Double–Stranded DNA Chain," 1995.

H. Isobe, et al., Database Chemical Abstract Online, AN 131:18823, XP–002170954, pps. 1–3, "Synthesis and Functions of a Novel DNA Binding Fullerene," 1999.

\* cited by examiner

*Primary Examiner*—Jezia Riley
(74) *Attorney, Agent, or Firm*—Oblon, Spivak, McClelland, Maier & Neustadt, P.C.

(57) ABSTRACT

A novel means for DNA compaction is provided.

The object is accomplished by providing a fullerene derivative having 1 to 4 nitrogen-containing hydrophilic side chain(s) or its salt for DNA compaction.

DNA compaction can be achieved effectively, and application to gene therapy is also expected.

24 Claims, 1 Drawing Sheet

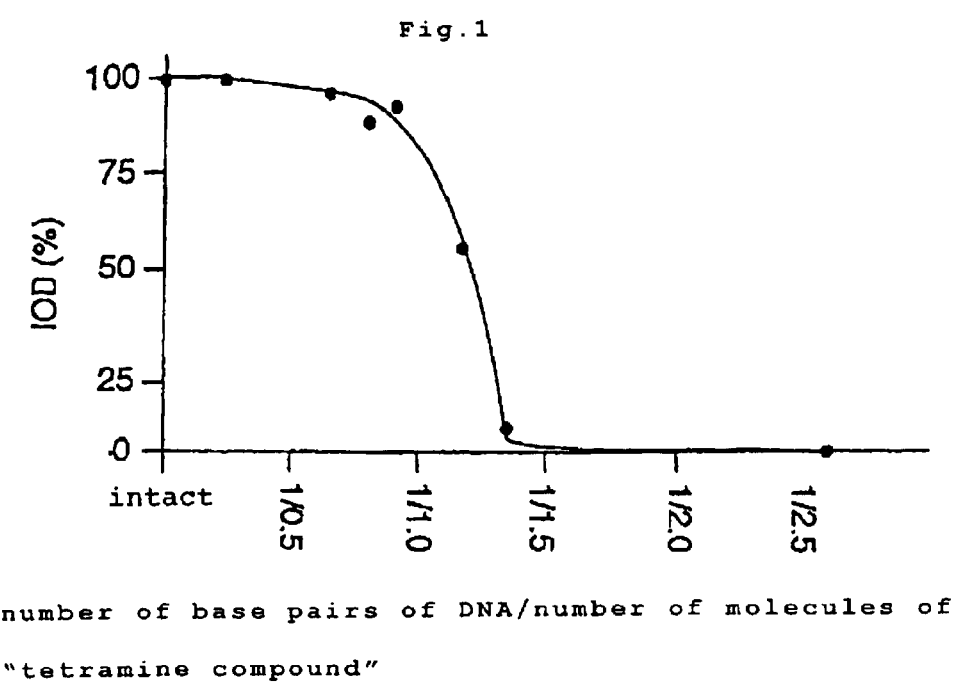

FULLERENE DERIVATIVES

TECHNICAL FIELD

The present invention relates to a fullerene derivative which has DNA compacting activity and is useful as a DNA compaction reagent, among other uses, and is applicable, for example, in the pharmaceutical industry.

BACKGROUND ART

DNA compaction in a protein-DNA complex such as the arrangement of DNAs on a chromosome is a very important subject of biochemical research. Compaction by organic micromolecules and inorganic ions is also an important subject of research relevant to transfection [e.g. Yoshikawa, Y. et al., FEBS Letters, 1996, vol. 396, 71–76; Behr, J-P, Acc. Chem. Res., 1993, vol. 26, 274–278; etc.].

The present invention has for its object to provide a novel means for DNA compaction.

DISCLOSURE OF INVENTION

Thus far has been provided a technology for use-tailored modification of fullerene, and a variety of fullerene derivatives have been synthesized [e.g. Friedman, S. H. et al. J. Am. Chem. Soc., 1993, vol. 115, 6506–6509; Yamago, S. et al., J. Am. Chem. Soc., 1994, vol. 116, 1123; Taki, M. et al., J. Am. Chem. Soc., 1997, vol. 119, 926; An, Y. Z. et al., Tetrahedron, 1996, vol. 52, 5179–5189; Nakamura, E. et al., Bull. Chem. Soc. Jpn., 1996, vol. 69, 2143–2151; Yamago, S. et al., Chemistry Letters, 1996, 395–396; Murata, Y. et al., The 2nd International Forum on Chemistry of Functional Organic Chemicals (IFOC-2), 1997, P-31, Tokyo, Japan, etc.].

The inventors of the present invention discovered that, among such fullerene derivatives, fullerene derivatives having 1 to 4, nitrogen-containing hydrophilic side chain(s), inclusive of salts thereof, are amphiphilic and have exceptionally high DNA-compacting activity and have accordingly developed the present invention.

1. Structure of the Fullerene Derivative of the Invention

The fullerene derivative of the present invention is a "fullerene derivative having 1 to 4, nitrogen-containing hydrophilic side chain(s)". This fullerene derivative includes not only novel compounds but also known compounds.

The DNA-compacting activity of the fullerene derivative of the present invention is the result of an interplay of the size and hydrophobicity of fullerene and the affinity of the nitrogen-containing hydrophilic side chain(s) of the derivative for the phosphate group. It is supposed that the interaction between fullerene and the hydrophobic moieties of a DNA (e.g. major grooves of the DNA) and the interaction between the nitrogen-containing hydrophilic side chain(s) and the phosphate group of the DNA causes the DNA unimolecule to be bent and folded, and that the hydrophobic moieties of a large number of such folded DNA unimolecules coalesce to cause said compaction.

Therefore, the molecular design of a fullerene derivative may be made liberally by one skilled in the art with the above mechanism taken into consideration. The DNA-compacting activity of the fullerene derivative synthesized accordingly can be evaluated by electrophoresis of a mixed solution of the fullerene derivative and a DNA (e.g. plasmid DNA) and measuring the amount of DNA. Moreover, since this compacting activity of the fullerene derivative is closely associated with the high binding affinity of the derivative for DNA, a screening can be made by an ethidium bromide displacement assay using calf thymus DNA.

While the fullerene derivative may be used in the form of a salt, the salt is preferably a conventionally nontoxic salt, particularly a pharmaceutically acceptable salt. More particularly, the salt includes inorganic acid salts (e.g. hydrochloride, hydrobromide, sulfate, phosphate, etc.), organic carboxylic acid or sulfonic acid salts (e.g. formate, acetate, trifluoroacetate, maleate, tartrate, fumarate, methanesulfonate, benzenesulfonate, toluenesulfonate, etc.), and salts with basic or acidic amino acids (e.g. arginine, aspartic acid, glutamic acid, etc.).

The fullerene derivative may occur as various isomers owing to the presence of asymmetric carbon and molecular asymmetry and any and all of them are subsumed under the concept of fullerene derivative according to the present invention.

The "fullerene" of the fullerene derivative of the present invention is not restricted to [60]fullerene but includes higher-order fullerenes (e.g. [70]fullerene etc.).

The preferred "nitrogen-containing hydrophilic side chain" includes "a hydrocarbon group which has 1 or 2 straight-chain or branched-chain substituent group(s) each comprising 1 to 10 nitrogen atom(s) and 2 to 30 carbon atoms, and is configured to be bonded to 1 or 2 of the 2 to 8 $sp^3$ carbon atoms present on the fullerene core". The more preferred is "a hydrocarbon group which has 1 or 2 straight-chain or branched-chain substituent group(s) each comprising 2 to 8 nitrogen atoms and 2 to 20 carbon atoms, and is configured to be bonded to two of the 2 to 8 $sp^3$ carbon atoms present on the fullerene core".

The amino group in said "nitrogen-containing hydrophilic side chain" may be primary, secondary or tertiary and may form a nitrogen-containing heterocyclic group [such as 3 to 8 (preferably 5 or 6)-membered unsaturated heteromonocyclic groups containing 1 to 4 nitrogen atom(s) (e.g. pyrrolyl, pyrrolinyl, imidazolyl, pyrazolyl, pyridyl, dihydropyridyl, pyrimidyl, pyrazinyl, pyridazinyl, triazolyl, tetrazolyl, etc.); and unsaturated fused heterocyclic groups containing 1 to 4 nitrogen atom(s) (e.g. indolyl, isoindolyl, indolidinyl, benzimidazolyl, quinolyl, isoquinolyl, indazolyl, benzotriazolyl, acridinyl, etc.)]. Furthermore, it may optionally be substituted by lower alkyl or the like.

The "nitrogen-containing hydrophilic side chain" mentioned above may have other hetero atoms, such as oxygen, sulfur, etc., as its constituent atoms and/or substituents.

Furthermore, when two or more "nitrogen-containing side chains" are present, there may be a cross-linking alkylene moiety bridging such nitrogen-containing hydrophilic side chains.

The "hydrocarbon group" of the "nitrogen-containing hydrophilic side chain" includes straight-chain, branched-chain, or cyclic hydrocarbon groups, whether saturated or unsaturated, and is preferably a hydrocarbon group of 1 to 20 carbon atom(s) (more preferably of 1 to 15 carbon atom(s)).

The specific structure of said "nitrogen-containing hydrophilic side chain" includes but is not limited to the following (the fullerene core is also shown).

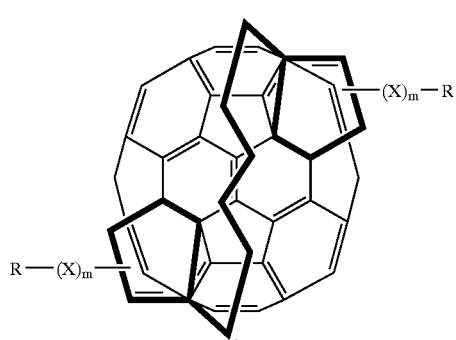
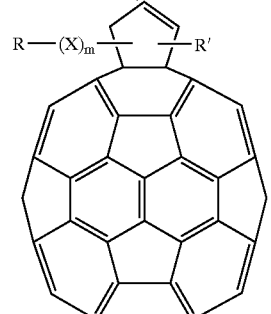
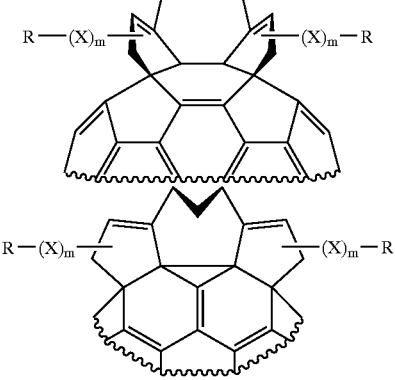
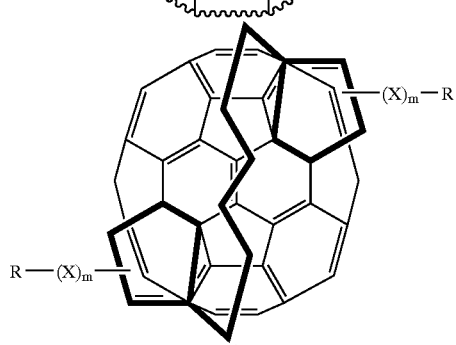
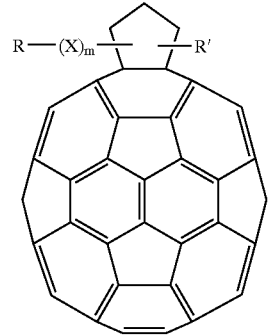
-continued
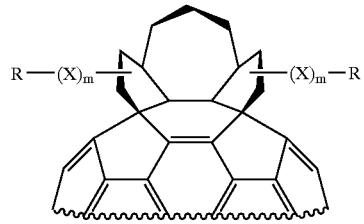
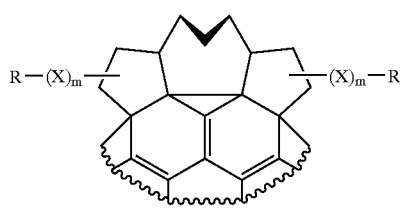
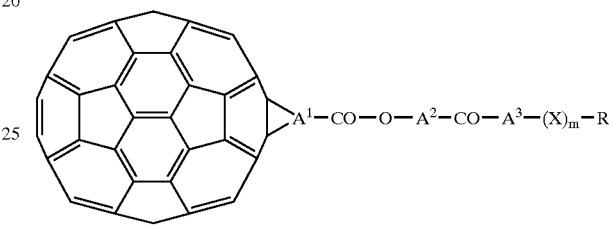
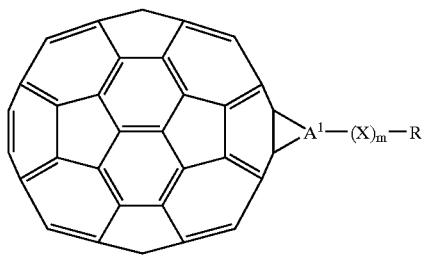
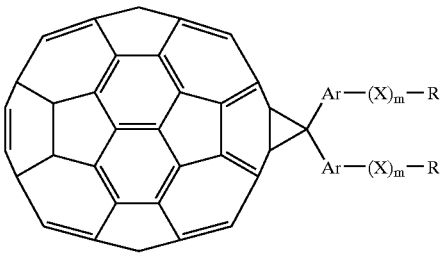
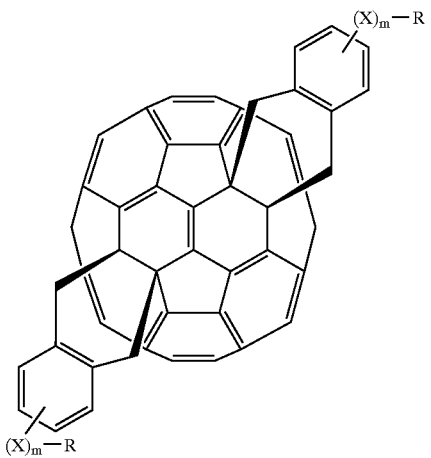

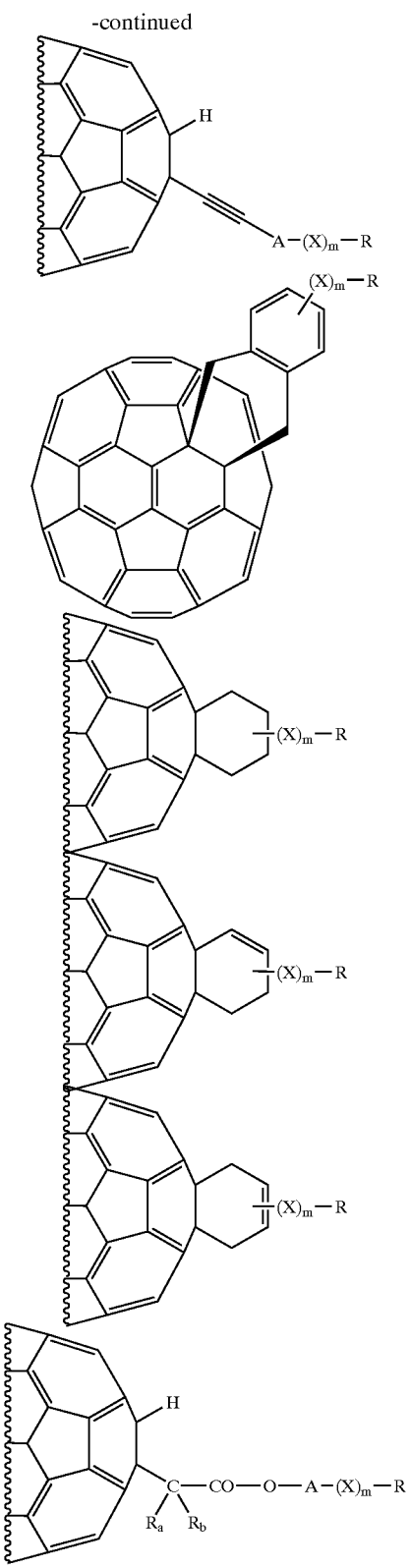

(lower)alkyl]amino(lower)alkanoyl groups, [N-pyrrolyl(lower)alkyl-N-(lower)alkyl]amino(lower)alkanoyl groups, [N-(N,N-di(lower)alkylamino)(higher)alkyl-N-(lower)alkyl]amino(lower)alkanoyl groups, [N-(N-(lower)alkylamino)(lower)alkyl-N-(lower)alkyl]amino(higher)alkanoyl groups, [N-pyrrolyl(higher)alkyl-N-(lower)alkyl]amino(higher)alkanoyl groups; groups of the formula:

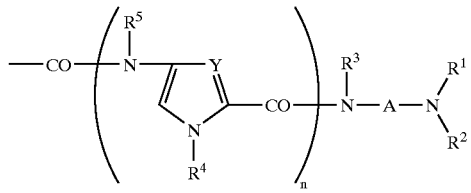

(wherein $R^1$, $R^2$, $R^3$, $R^4$ and $R^5$ may each be the same or different over its occurrences and represents hydrogen or a lower alkyl group; A represents an alkylene group; Y represents CH or N, and n represents an integer of 1 to 4)]; straight-chain or branched-chain $C_{2-30}$ alkyl groups comprising 1 to 10 nitrogen atom(s) and 2 to 30 carbon atoms [more preferably [N-(N,N-di(lower)alkylamino)(lower)alkyl-N-(lower)alkyl]amino(lower)alkyl groups, [N-(N-(lower)alkylamino)(lower)alkyl-N-(lower)alkyl]amino(lower)alkyl groups, [N-pyrrolyl(lower)alkyl-N-(lower)alkyl]amino(lower)alkyl groups, [N-(N,N-di(lower)alkylamino)(higher)alkyl-N-(lower)alkyl]amino(lower)alkyl groups, [N-(N-(lower)alkylamino)(lower)alkyl-N-(lower)alkyl]amino(higher)alkyl groups, [N-pyrrolyl(higher)alkyl-N-(lower)alkyl]amino(higher)alkyl groups; or groups of the formula:

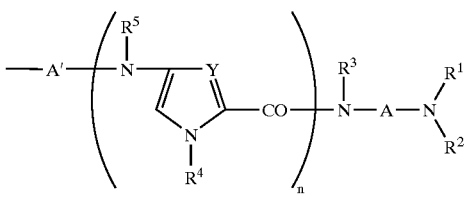

(wherein $R^1$, $R^2$, $R^3$, $R^4$, $R^5$, A, Y and n are respectively as defined above; A' represents an alkylene group)].

Ar represents an aryl group (e.g. phenyl, naphthyl, anthryl, etc.);

R' represents hydrogen or a lower alkyl group;

Ra and Rb may be the same or different and each represents hydrogen or a lower alkyl group, or Ra and Rb may, jointly and taken together with the carbon atom to which they are joined, represent a 3 to 6-membered cycloalkyl group.

A, $A^1$, $A^2$ and $A^3$ may be the same or different and each represents an alkylene group;

X represents —O—, —N— or —S—; and m represents an integer of 0 or 1.

It should, however, be understood that the various "nitrogen-containing hydrophilic side chains" mentioned above are mere examples and, as the structure interposed between "the fullerene core" and "the group of the formula

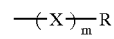

the various known structures other than those illustrated above may also be selectively used.

In the above formulas, Rs may be the same or different and each represents a straight-chain or branched-chain acyl group comprising 1 to 10 nitrogen atom(s) and 2 to 30 carbon atoms [more preferably [N-(N,N-di(lower)alkylamino)(lower)alkyl-N-(lower)alkyl]amino(lower)alkanoyl groups, [N-(N-(lower)alkylamino)(lower)alkyl-N-

The "lower alkyl group" or "lower alkyl moiety" in the context of the present invention includes straight-chain or branched-chain groups each containing 1 to 6 carbon atom (s), such as methyl, ethyl, propyl, isopropyl, butyl, isobutyl, sec-butyl, tert-butyl, pentyl, isopentyl, tert-pentyl, neopentyl, hexyl, isohexyl, etc.

The "alkylene group" includes straight-chain or branched-chain groups containing 1 to 10 carbon atom(s), such as methylene, ethylene, trimethylene, 2-methyltrimethylene, tetramethylene, ethylethylene, pentamethylene, 3-methylpentamethylene, hexamethylene, 2-ethyltetramethylene, heptamethylene, octamethylene, nonamethylene, decamethylene, etc.

The "higher alkyl group" or "higher alkyl moiety" includes straight-chain or branched-chain groups each containing 7 to 20 carbon atoms, such as heptyl, octyl, 2-ethylhexyl, nonyl, decyl, 3,7-dimethyloctyl, undecyl, dodecyl, tridecyl, tetradecyl, pentadecyl, 3-methyl-10-ethyldodecyl, hexadecyl, heptadecyl, octadecyl, nonadecyl, eicosyl, etc.

The number of "nitrogen-containing hydrophilic side chains" on the fullerene core is preferably 1 to 4, and the presence of one or two such side chains is particularly preferred. When only one side chain is to be used, it is preferable to select a side chain containing a relatively large number of nitrogen atoms (preferably 4 or more N atoms). Particularly preferred is a polypyrrole which has a comparatively high binding affinity. When two side chains are to be involved, the use of alkylpolyamines containing 2 to 8 nitrogen atoms, which are comparatively less hydrophilic, is preferred.

Among the various fullerene derivatives described above, suitable derivatives can be judiciously selected in consideration of the ease of synthesis and the binding affinity for DNA, among other factors, but based on the information so far available, derivatives of the following general formula (I), inclusive of salts thereof, can be mentioned as preferred examples.

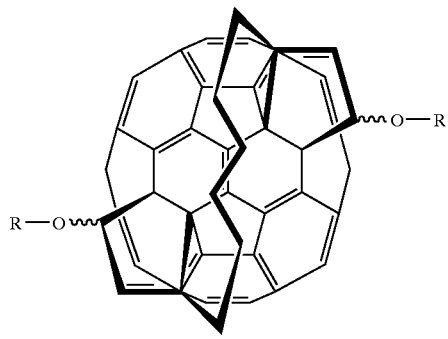

[wherein the two Rs may be the same or different and each represents a straight-chain or branched-chain acyl group comprising 1 to 10 nitrogen atom(s) and 2 to 30 carbon atoms or hydrogen (provided, however, that the two Rs do not concurrently represent hydrogen)].

As the more preferred examples of the fullerene derivative, there can be mentioned derivatives of general formula (I) wherein the two Rs are the same or different and each represents a straight-chain or branched-chain acyl group comprising 2 to 8 nitrogen atoms and 2 to 30 carbon atoms as its constituent atoms.

As the still more preferred examples of the fullerene derivative, there can be mentioned derivatives of general formula (I) wherein the two Rs are the same or different and each represents a straight-chain or branched-chain acyl group comprising 2 to 8 nitrogen atoms and 2 to 20 carbon atoms as its constituent atoms.

Furthermore, fullerene derivatives of the following general formula (II):

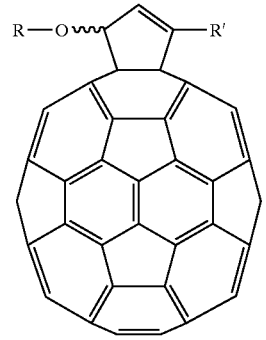

[wherein R represents a straight-chain or branched-chain acyl group comprising 1 to 10 nitrogen atom(s) and 2 to 30 carbon atoms and R' represents hydrogen or a lower alkyl group] inclusive of salts thereof can also be mentioned as preferred examples of the fullerene derivative.

As the more preferred examples of the fullerene derivative, there can be mentioned derivatives of general formula (II) wherein R represents a straight-chain or branched-chain acyl group comprising 2 to 8 nitrogen atoms and 2 to 30 carbon atoms.

The still more preferred examples of the fullerene derivative are derivatives of general formula (II) wherein R represents a straight-chain or branched-chain acyl group comprising 2 to 8 nitrogen atoms and 2 to 20 carbon atoms.

2. Method of Producing the Fullerene Derivative of the Invention

The above-mentioned fullerene derivatives and salts of the present invention can be synthesized by the processes known to those skilled in the art, either as such or as appropriately modified, according to the respective structures desired [cf. the literature cited above or below].

The method of producing the fullerene derivative of the invention is now described in further detail, taking fullerene derivatives having one or two nitrogen-containing hydrophilic side chains" as examples.

Process A (One Side Chain)

The organofullerene (methanofullerene, propanofullerene) obtainable by carrying out the known reaction of the vinylcarbene species thermally generated from a cyclopropenone acetal with fullerene (Literature 1; Tokuyama, H.; Isobe, H.; Nakamura, E., Bull. Chem. Soc. Jpn. 1995, vol. 68, 935–941) is subjected to a functional group transformation reaction to introduce a nitrogen-containing side chain. Methanofullerene and propanofullerene are respectively converted to hydroxy-containing organofullerenes, by the procedure which comprises adding water after the reaction of said vinylcarbene species to hydrolyze the ketene acetal in the case of methanofullerene and by the procedure which comprises hydrolytic removal of the acetal with the aid of the sulfuric acid catalyst in water/tetrahydrofuran/chlorobenzene and subsequent reduction with diisobutylaluminum hydride. The objective fullerene derivative can be synthesized by subjecting the thus-generated hydroxyl group to the following functional group transformation.

1. Known reaction (Literature 2, Nakamura, E.; Tokuyama, H.; Yamago, S.; Shiraki, T.; Sugiura, Y., Bull. Chem. Soc. Jpn. 1996, vol. 69, 2143–2151). By the coupling reaction of succinic anhydride and a hydroxy-containing organofullerene, the carboxylic acid derivative is prepared. This carboxylic acid and an amine compound having a primary or secondary amino function are subjected to coupling reaction to give the objective product.

As the amine compound mentioned just above, a polypyrrole derivative analogous to the netropsin derivative described in Literature 2, a polyamine such as an alkylspermidine or the like, and even acridine or the like which is intercalatable into the DNA base pair can be employed, for instance.

2. An α-haloacid halide is coupled to a hydroxyl group-containing organofullerene (Literature 3: Boutorine, A. S.; Tokuyama, H.; Takasugi, M.; Isobe, H.; Nakamura, E.; Helene, C., Angew. Chem., Int. Ed. Engl., 1994, vol. 33, 2462–2465; Literature 4: An, Y. Z.; Chen, C. H. B.; Anderson, J. L. Sigman; D. S. Foote, C. S.; Rubin, Y., Tetrahedron, 1996, vol. 52, 5179–5189) to give an α-halocarbonyl compound. The objective product can be obtained by coupling this halide to an amine compound having a primary or secondary amino function.

As this amine compound, the specific amine compounds mentioned hereinbefore can be employed.

These procedures can be applied to the known hydroxy-containing fullerene derivatives (Literature 4 cited above; Literature 5: Tokuyama, H.; Yamago, S., Nakamura, E.; Shiraki, T.; Sugiura, Y., J. Am. Chem. Soc., 1993, vol. 115, 7918–7919) in common.

Process B (2 Side Chains)

A fullerene derivative having more potent DNA-compacting activity can be synthesized from an organofullerene (bispropanofullerene) obtained by carrying out the known reaction of a biscyclopropenone acetal with a fullerene (Literature 6: Isobe, H.; Tokuyama, H.; Sawamura, M.; Nakamura, E., J. Org. Chem. 1997, vol. 62, 5034–5041) in conjunction with the procedure of said Process A by subjecting it to functional group transformation to thereby introduce hydrophilic residues. The functional group transformation of bispropanofullerene is carried out, just as mentioned above, by the hydrolytic removal of the acetal in the presence of the sulfuric acid catalyst in water/tetrahydrofuran/chlorobenzene and subsequent reduction with diisobutylaluminum hydride, whereby the bispropanofullerene is converted to an organofullerene having a couple of hydroxyl groups. In this procedure, a mixture of 8 different isomers inclusive of diastereomers is obtained, and the objective fullerene derivative can be synthesized by subjecting this mixture to the same functional group transformation as above.

1. Succinic anhydride is coupled to a hydroxy-containing organofullerene to give the carboxylic acid derivative. This carboxylic acid is coupled to an amine compound having a primary or secondary amino function to obtain the desired product.

As the amine compound, the same specific compounds as mentioned above can be employed.

2. An α-haloacid halide is coupled to an organofullerene having two hydroxyl groups to give the corresponding α-halocarbonyl compound. As the α-haloacid halide for use in this procedure, α-bromoacetyl bromide is known. As the halide, both the chloride and the bromide can be utilized and even the compound bearing a substituent in the α-position can also be used. Regarding the organofullerene, a report is available on the derivatives having the $C_2$ symmetry (Literature 7: Isobe, H.; Sawamura, M.; Nakamura, E., 13th Fullerene Symposium, 1997, 2–20, Nagano, Japan) but the equivalent or higher activity may be obtained by using organofullerenes of other symmetries as described in the above-cited Literature 6 or a mixture of isomers obtainable by said reduction with diisobutylaluminum hydride. The coupling of the resulting halide to an amine compound having a primary or secondary amino function, such as the compound mentioned above, gives the objective product.

The above amine compound includes the species mentioned hereinbefore.

The above procedures can be applied to any known fullerene derivatives having a plurality of hydroxyl groups (Literature 8: Taki, M.; Sugita, S.; Nakamura, Y.; Kasashima, E.; Yashima, E.; Okamoto, Y.; Nishimura, J., J. Am. Chem. Soc., 1997, vol. 119, 926) as well.

Those skilled in the art should be able to produce fullerene derivatives having desired structures in accordance with the invention by referring to the disclosures in the literature cited in this specification, known technologies, and the specific disclosures concerning Processes A and B, or working examples which are presented hereinafter.

3. Modes of Use of the Fullerene Derivative of the Invention

The fullerene derivative of the present invention is an amphiphilic compound having excellent DNA-compacting activity. Permitting the fullerene derivative of the invention to act on DNA leads to the result that the derivative binds the DNA and the unimolecular DNA is bent and folded by the interbinding force acting between the intramolecular double strands. Furthermore, by the intermolecular binding force, a DNA condensate is produced. This compaction is reversible with respect to the concentration of the fullerene derivative and the regeneration of the DNA takes place upon extractive removal of the fullerene derivative.

The foregoing has been confirmed by the agarose electrophoretic analysis and AFM microscopic morphological observation of samples prepared by causing a varying concentration of the "tetramine compound", to be described below, to act upon the plasmid pBR322. This will be explained below using specific experimental data.

Test Compound

The fullerene derivative obtained in Example 1 which appears below (hereinafter referred to as "tetramine compound") was submitted to the experiment.

Electrophoresis Experiment Protocol

Electrophoresis was carried out in accordance with the method described in Short Protocols in Molecular Biology 3rd E., 1992, Wiley, 2–13.

As test samples, solutions prepared by dissolving the plasmid $pBR^{322}$ (25 μg/mL) and various amounts of "tetramine compound" in 20% THF/HEPES-Mg buffer (20 μL) were used. Each sample was incubated at 25° C. for 5 minutes and then developed on an agarose gel using a buffer solution (5 μL) containing 0.25% (w/v) Bromophenol Blue and 50% (v/v) glycerol. Electrophoresis was carried out using an ethidium bromide (0.5 mg/mL)-containing 1% (w/v) agarose gel/TBE buffer solution. The integrated optical density (IOD) of the fluorescent emission photograph was measured using NIH Image Program vl. 60. By this method, the migration amount of DNA was determined.

Results

The details are shown in FIG. 1.

Depending on the concentration of "tetramine compound", a phase transition phenomenon occurred. Thus, the amount of DNA migration in agarose electrophoresis declined rapidly when the ratio of the number of molecules of fullerene derivative to the number of base pairs of DNA was 1/1 and became nil at 1/2.6.

In the AFM microscopic observation of the same samples in a thin film of water, quite dissimilar AFM images were obtained before and after phase transition. Compaction of the DNA began before onset of phase transition and it was confirmed that the polymolecular compact obtained after phase transition was a hydrophobic mass.

The above experimental results suggest that in order that a wholesome DNA compact may be formed, the ratio of the number of molecules of the fullerene derivative to the number of base pairs of DNA preferably lies within the range of 4:1 to 1:2.

The above formation of a DNA condensate by the fullerene derivative is carried out by mixing the two reactants in a suitable buffer. However, this is not an exclusive choice but any other method in routine use in the art can be employed. Moreover, the DNA condensate formed can be isolated by the routine procedure, for example by subjecting the DNA solution after phase transition to ethanol precipitation. Furthermore, by extracting the fullerene derivative from the solution of DNA which has been compacted by addition of the derivative with an organic solvent such as chloroform, regeneration of the original DNA can be achieved.

As mentioned hereinbefore, the DNA-compacting activity of the fullerene derivative is closely associated with its high binding affinity for DNA. For reference, results of a relevant experiment with said "tetramine compound" are shown below.

Experimental Method

DNA-compacting activity was evaluated in an ethidium bromide displacement assay. This competitive binding assay was carried out according to the protocol described in Journal of Medicinal Chemistry, 21, 658–668 (1978).

Results

The "tetramine compound" at a concentration of 1.9 $\mu$M substituted 50% of ethidium bromide.

This result can be used as a reference in the molecular designing of a fullerene derivative which is particularly useful for carrying the present invention into practice and a derivative having an equivalent or higher binding affinity for DNA as compared with the compound mentioned just above is especially desirable.

For exploring into the mechanism of DNA compaction by the fullerene derivative of the invention, the following two experiments were performed.

Experimental Method

Measurement of the CD Spectrum

A solution of calf thymus DNA (average MW=8.6 MDa, 13 kbp, 42% GC, highly polymerized, type 1, Sigma) or plasmid pBR322 DNA (MW=2.83 MDa, 4361 bp, New England Biolabs) in HEPES-Mg buffer (40 mM HEPES, 10 mM MgCl2; pH=7.6) at a base-pair concentration of 100 mM was prepared and put in a quartz glass cell, and using a JASCO J-720 spectrometer the CD spectrum was measured at 25° C. Furthermore, the nucleic acid-compacting fullerene derivative was added to the above solution at concentrations 10 to 200 mM and the CD spectra were measured.

Results

No change at all occurred in the DNA conformational CD spectra, indicating that the DNA retained the B-form.

Experimental Method

Measurement of DNA Melting Temperature (Tm)

A solution of calf thymus DNA (average MW=8.6 MDa, 13 kbp, 42% GC, highly polymerized, type 1, Sigma) in HEPES-Mg buffer (40 mM HEPES, 10 mM MgCl2; pH=7.6) at a base-pair concentration of 100 mM was prepared and the nucleic acid-compacting fullerene was added at a concentration of 10 mM.

The above solution was put in a quartz glass cell and while the temperature was raised from 60° C. at a rate of 1° C./min, the absorbance at the wavelength of 258 nm where the hypochromism of a DNA double-strand is observed, was measured with a JASCO J-720 spectrometer.

Results

The melting temperature of the double-strand was increased by 2.7° C. to 74.2° C. as compared with the case in which the nucleic acid-compacting fullerene was not added (71.5° C.), indicating stabilization of the double-stranded structure.

The above experimental results strongly suggested the mechanism that the DNA unimolecule is folded as the result of an interaction between the nucleic acid-compacting fullerene and the hydrophobic moiety of DNA (e.g. the major grooves of a DNA) and an interaction between the nitrogen-containing hydrophilic side chain and the phosphate group of the DNA, and that the hydrophobic moieties of a large number of folded DNA unimolecules coalesce to cause said compaction.

It is quite a novel finding that the fullerene derivative of the present invention not only has a binding affinity for DNA but even has an ability to compact a polymolecular DNA.

Therefore, "the mode of use for DNA compaction" and the mode of use as a "DNA compaction reagent" of the present invention include all possible embodiments exploiting the DNA-compacting activity of the fullerene derivative of the invention described hereinbefore. Included, among such embodiments, are the use as a DNA compaction reagent; use for introduction of a vector into cells; use for introduction of a DNA (or a derivative thereof) fragment such as an antisense DNA (or a derivative thereof) or a decoy DNA (or a derivative thereof) into cells; use for control of gene expression through the binding to a promoter or enhancer region; use for modulating the cell cycle through suppression of the conversion of a double-stranded DNA to a single-stranded DNA; and use for control of the PCR efficiency through adjustment of the melting point involved in the transition from a single-stranded DNA to a double-stranded DNA or from a double-stranded DNA to a single-stranded DNA. Furthermore, application to gene therapies is also within the purview.

In using the fullerene derivative in any of the above modes of use, the fullerene derivative or salt of the invention can be used as it is or in the form of a composition to accomplish the intended object.

EXAMPLES

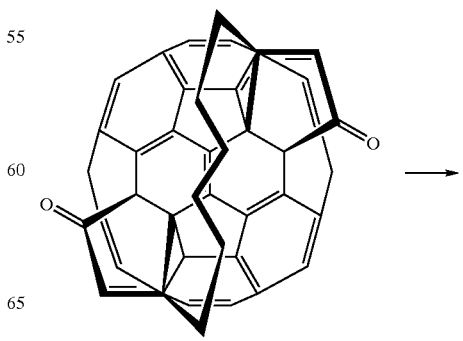

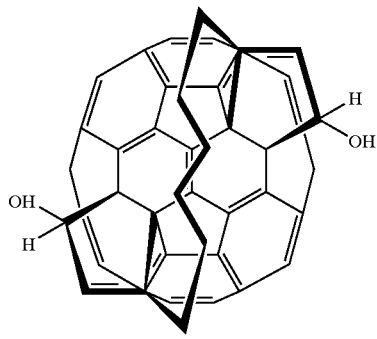

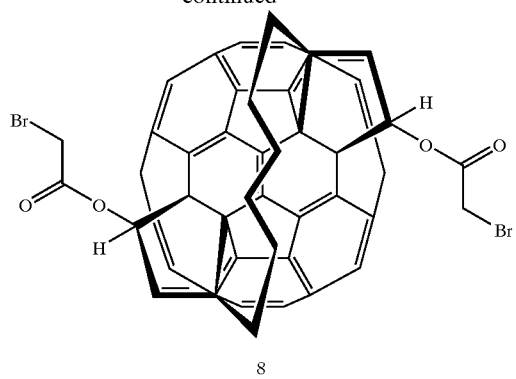

hydride (in hexane) (0.95 M, 751 μL) slowly at room temperature. After 2 hours of constant stirring, a 30% aqueous solution of potassium sodium tartrate was added, and the mixture was stirred for 1 hour. The crude solution was washed with water, and removal of organic solvent in vacuo gave a crude product as a sparingly soluble black solid mass (130 mg). This diol 7 is a mixture of $C_2$ symmetric and $C_1$ symmetric diastereomers (about 7:3). This mixture is not further purified but submitted directly to the subsequent reaction.

Diol 7;

$R_f$=0.15 (PhCl);

IR (KBr): 3417, 2925, 1506, 798, 694 cm$^{-1}$;

$^1$H NMR (400 MHz, CDCl$_3$/CS$_2$1/1) δ 1.54–1.62 (br m, 4H, (CH$_2$)$_2$—(CH$_2$)$_2$—(CH$_2$)$_2$), 1.76–1.88 (br m, 2H, homoallylic methylene proton), 1.88–1.99 (br m, 2H, homoallylic methylene proton), 2.28 (d, 2H, J=12.0 Hz, OH), 2.65–2.80 (m, 4H, allylic methylene proton), 6.22 (br s, 2H, vinyl proton), 6.34 (br d, 2H, J=12.0 Hz, allylic methylene proton).

Preparation 2

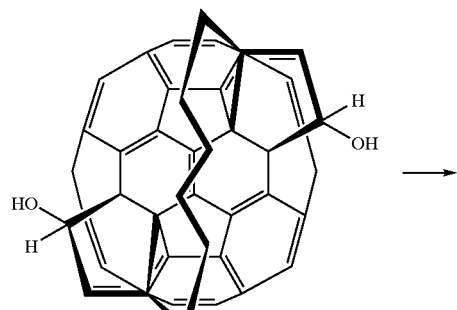

7

To a solution of diol 7 (50 mg, 54.7 μmol) in chlorobenzene (50 mL) were added bromoacetyl bromide (23.7 μL, 274 μmol) and pyridine (22.1 μL, 274 μmol). After 6 hours of constant stirring, the reaction was stopped by adding sodium hydrogen carbonate. Extraction with water gave a crude product. Purification by silica gel column chromatography (silica gel 5 g, elution with chlorobenzene) gave dibromide 8 (31.6 mg, 50%, 2 steps).

Dibromide 8;

$R_f$=0.65 (PhCl);

IR (KBr): 2925, 2954, 1733, 1261, 694 cm$^{-1}$;

$^1$H NMR (400 MHz, CDCl$_3$) δ 1.55–1.63 (br m, 4H, (CH$_2$)$_2$—(CH$_2$)$_2$—(CH$_2$)$_2$), 1.80–2.00 (br m, 4H, homoallylic methylene proton), 2.70–2.84 (br m, 4H, allylic methylene proton), 3.80 (d, 2H, J=12.0 Hz, BrCH$_2$CO), 3.84 (d, 2H, J=12.0 Hz, BrCH$_2$CO), 6.16 (br s, 2H, vinyl proton), 7.33 (br s, 2H, allylic methylene proton);

$^{13}$C NMR (100 MHz, CDCl$_3$) δ 25.66 (CH$_2$), 27.03 (CH$_2$), 29.33 (CH$_2$), 73.11 (sp$^3$, C60), 74.11 (sp$^3$, C60), 88.04 (allylic CH), 125.05 (vinyl CH), 127.24, 132.98, 136.38, 136.52, 138.30, 139.56, 141.79, 141.93, 142.07, 142.11, 143.14, 144.74, 144.76, 144.90, 145.32, 145.41, 145.62, 145.67, 146.01, 146.05, 146.35, 147.36, 147.61, 147.83, 148.34, 148.74, 148.98, 149.87, 152.51, 166.78 (C=O).

Example 1

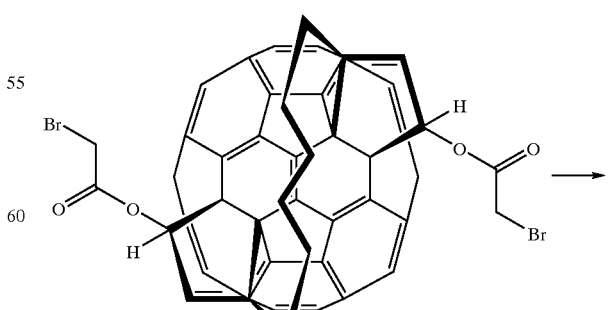

8

-continued

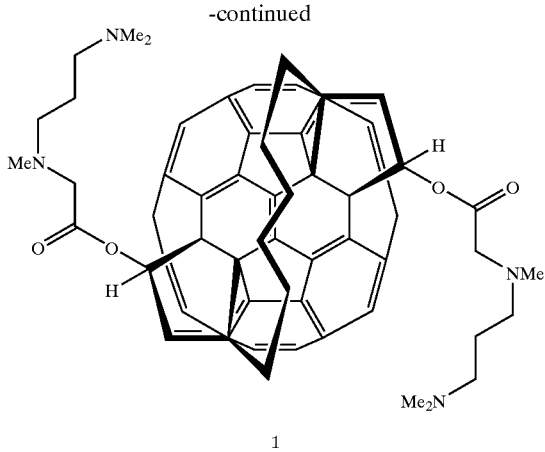

1

To a solution of dibromide 8 (23.1 mg, 20.0 μmol) in chlorobenzene (10 mL) was added N,N,N'-trimethyl-1,3-propanediamine (14.7 μL, 100 μmol). After 1 hour of constant stirring, aqueous extraction was carried out to give a crude product. Purification by gel permeation chromatography (JAIGEL-1H 20×600 mm and -2H 20×600 mm GPC columns, elution with 0.5% triethylamine/chloroform) gave tetramine 1 (12.2 mg, 50%).

Tetramine 1;

$R_f$=0.05 (CHCl$_3$/MeOH/AcOH 85/10/5);

$^1$H NMR (400 MHz, CDCl$_3$) δ 1.40–1.54 (overlapped m, 8H, NCH$_2$CH$_2$ and (CH$_2$)$_2$—(CH$_2$)$_2$—(CH$_2$)$_2$), 1.50–1.75 (br m, 2H, homoallylic methylene proton), 1.75–2.00 (br m, 2H, homoallylic methylene proton), 2.08 (overlapped s, 16H, N(CH$_3$)$_2$ and NCH$_2$), 2.20 (s, 6H, NCH$_3$), 2.36 (t, 4H, J=7.4 Hz, NCH$_2$), 2.60–2.74 (br m, 4H, allylic methylene proton), 3.15 (d, 2H, J=17.2 Hz, NCH$_2$CO), 3.28 (d, 2H, J=17.2 Hz, NCH$_2$CO), 6.08 (br s, 2H, vinyl proton), 7.35 (br s, 2H, allylic methylene proton);

$^{13}$C NMR (100 MHz, CDCl$_3$) δ 25.53 (CH$_2$), 25.96 (CH$_2$), 26.91 (CH$_2$), 29.29 (CH$_2$), 42.09 (NCH$_3$), 45.55 (N(CH$_3$)$_2$), 54.63 (CH$_2$), 57.55 (CH$_2$), 58.30 (CH$_2$), 73.28 (sp$^3$, C60), 74.08 (sp$^3$, C60), 86.68 (allylic CH), 125.86 (vinyl CH), 127.24, 132.76, 136.34, 136.40, 138.19, 139.49, 141.80, 141.83, 141.86, 142.08, 143.17, 144.65, 144.73, 144.97, 145.20, 145.44, 145.46, 145.65, 145.96, 145.99, 146.29, 147.52, 147.82, 148.71, 148.91, 148.96, 150.23, 151.21, 155.30, 170.68 (C=O).

BRIEF DESCRIPTION OF THE DRAWING

FIG. 1 shows the result of an experiment in which the "tetramine compound" was subjected to agarose gel electrophoresis. The ordinate represents IOD (%) and the abscissa represents the ratio of the number of molecules of the "tetramine compound" to the number of base pairs of DNA.

What is claimed is:

1. A method of transfection of DNA into cells, comprising contacting DNA with a fullerene derivative having 1 to 4 nitrogen-containing hydrophilic side chains or a salt thereof in the presence of cells.

2. The method of claim 1, wherein said nitrogen-containing hydrophilic side chain is a hydrocarbon group which has 1 or 2 straight-chain or branched-chain substituent groups each comprising 1 to 10 nitrogen atoms and 2 to 30 carbon atoms, and is bonded to 1 or 2 of the 2 to 8 sp$^3$ carbon atoms present on the fullerene core, with the proviso that there may exist a cross-linking moiety comprising an alkylene group bridging two or more nitrogen-containing hydrophilic side chains.

3. The method of claim 1, wherein said fullerene derivative or salt thereof has one or two nitrogen-containing hydrophilic side chains.

4. The method of claim 1, wherein said fullerene derivative contains a nitrogen-containing hydrophilic side chain which is a hydrocarbon group which has 1 or 2 straight-chain or branched-chain substituent groups each comprising 2 to 8 nitrogen atoms and 2 to 20 carbon atoms, and is bonded to two of the 2 to 8 sp$^3$ carbon atoms present on the fullerene core, with the proviso that there may exist a cross-linking moiety comprising an alkylene group bridging two nitrogen-containing hydrophilic side chains.

5. The method of claim 1, wherein said fullerene derivative and said DNA are contacted in a relative amount such that a ratio of molecules of said fullerene derivative to base pairs of DNA is within 4:1 to 1:2.

6. The method of claim 1, wherein said fullerene derivative has the following general formula or a salt thereof:

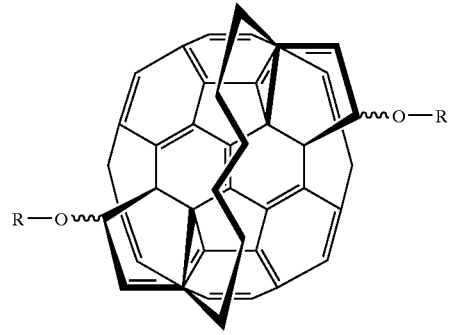

wherein the two Rs may be the same or different and each represents a straight-chain or branched-chain acyl group comprising 1 to 10 nitrogen atoms and 2 to 30 carbon atoms or hydrogen, with the proviso that the two Rs are not both hydrogen.

7. The method of claim 6, wherein the two Rs are the same or different and each represents a straight-chain or branched-chain acyl group comprising 2 to 8 nitrogen atoms and 2 to 20 carbon atoms.

8. The method of claim 6, wherein the two Rs are the same or different and each represents a [N-(N,N-di(lower)alkylamino)(lower)alkyl)-N-(lower)alkyl]amino(lower)alkanoyl group.

9. The method of claim 1, wherein said fullerene derivative has the following general formula or a salt thereof:

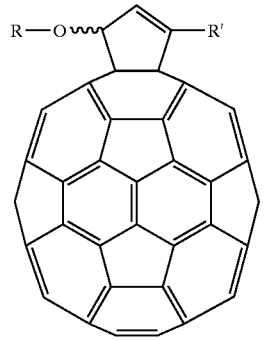

wherein R represents a straight-chain or branched-chain acyl group comprising 1 to 10 nitrogen atoms and 2 to 30 carbon atoms and R' represents hydrogen or a lower alkyl group.

10. The method of claim 9, wherein R represents a straight-chain or branched-chain acyl group comprising 2 to 8 nitrogen atoms and 2 to 20 carbon atoms.

11. The method of claim 9, wherein R is an [N-(N,N-di(lower)alkylamino)(lower)alkyl-N-(lower)alkyl]amino(lower)alkanoyl group.

12. The method of claim 1, which comprises compacting said DNA by contacting said DNA with said fullerene derivative or a salt thereof in the presence of cells.

13. The method of claim 12, wherein said nitrogen-containing hydrophilic side chain is a hydrocarbon group which has 1 or 2 straight-chain or branched-chain substituent groups each comprising 1 to 10 nitrogen atoms and 2 to 30 carbon atoms, and is bonded to 1 or 2 of the 2 to 8 $sp^3$ carbon atoms present on the fullerene core, with the proviso that there may exist a cross-linking moiety comprising an alkylene group bridging two or more nitrogen-containing hydrophilic side chains.

14. The method of claim 12, wherein said fullerene derivative or salt thereof has one or two nitrogen-containing hydrophilic side chains.

15. The method of claim 12, wherein said fullerene derivative contains a nitrogen-containing hydrophilic side chain which is a hydrocarbon group which has 1 or 2 straight-chain or branched-chain substituent groups each comprising 2 to 8 nitrogen atoms and 2 to 20 carbon atoms, and is bonded to two of the 2 to 8 $sp^3$ carbon atoms present on the fullerene core, with the proviso that there may exist a cross-linking moiety comprising an alkylene group bridging two nitrogen-containing hydrophilic side chains.

16. The method of claim 12, wherein said fullerene derivative and said DNA are contacted in a relative amount such that a ratio of molecules of said fullerene derivative to base pairs of DNA is within 4:1 to 1:2.

17. The method of claim 12, wherein said fullerene derivative has the following general formula or a salt thereof:

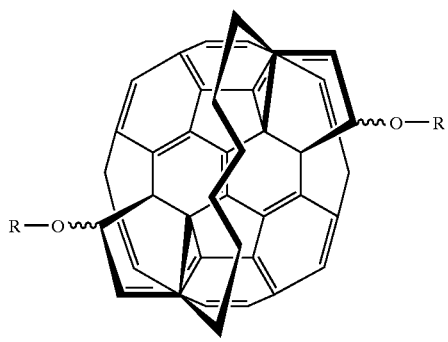

wherein the two Rs may be the same or different and each represents a straight-chain or branched-chain acyl group comprising 1 to 10 nitrogen atoms and 2 to 30 carbon atoms or hydrogen, with the proviso that the two Rs are not both hydrogen.

18. The method of claim 17, wherein the two Rs are the same or different and each represents a straight-chain or branched-chain acyl group comprising 2 to 8 nitrogen atoms and 2 to 20 carbon atoms.

19. The method of claim 17, wherein the two Rs are the same or different and each represents a [N-(N,N-di(lower)alkylamino)(lower)alkyl-N-(lower)alkyl]amino(lower)alkanoyl group.

20. The method of claim 12, wherein said fullerene derivative has the following general formula or a salt thereof:

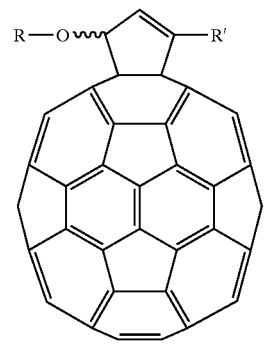

wherein R represents a straight-chain or branched-chain acyl group comprising 1 to 10 nitrogen atoms and 2 to 30 carbon atoms and R' represents hydrogen or a lower alkyl group.

21. The method of claim 20, wherein R represents a straight-straight-chain or branched-chain acyl group comprising 2 to 8 nitrogen atoms and 2 to 20 carbon atoms.

22. The method of claim 20, wherein R is an [N-(N,N-di(lower)alkylamino(lower)alkyl-N-(lower)alkyl]amino(lower)alkanoyl group.

23. The method of claim 1, wherein said contacting of said DNA with said fullerene derivative is carried out in a buffer.

24. The method of claim 12, wherein said contacting of said DNA with said fullerene is carried out in a buffer.

* * * * *